United States Patent [19]
Laping et al.

[11] Patent Number: 6,127,522
[45] Date of Patent: Oct. 3, 2000

[54] CRFG-1A, A TARGET AND MARKER FOR CHRONIC RENAL FAILURE

[75] Inventors: Nicholas J Laping, West Chester; Barbara Olson, Norristown; Yuan Zhu, Blue Bell, all of Pa.

[73] Assignee: SmithKline Beecham Corporation, Philadelphia, Pa.

[21] Appl. No.: 09/192,659

[22] Filed: Nov. 16, 1998

Related U.S. Application Data

[62] Division of application No. 09/020,466, Feb. 9, 1998, Pat. No. 5,879,908.
[60] Provisional application No. 60/045,203, Apr. 30, 1997.
[51] Int. Cl.$^7$ ..................................................... C07K 14/00
[52] U.S. Cl. ........................................... 530/350; 530/300
[58] Field of Search ...................................... 530/350, 300

[56] References Cited

PUBLICATIONS

HGS EST #682636.

*Primary Examiner*—Karen Cochrane Carlson
*Attorney, Agent, or Firm*—Elizabeth J. Hecht; Ratner & Prestia; William T. King

[57] ABSTRACT

CRFG-1a polypeptides and polynucleotides and methods for producing such polypeptides by recombinant techniques are disclosed. Also disclosed are methods for utilizing CRFG-1a polypeptides and polynucleotides in the design of protocols for the treatment of chronic renal disease, renal ischemia, diabetic nephropathy, acute renal failure, Neurodegenerative disease, and Alzeimer's disease, among others, and diagnostic assays for such conditions.

2 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2371 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AGCATGGCAC ATTACAACTT CAAGAAAATT ACGGTGGTGC CGTCCGCCAA GGACTTCATA        60

GACCTCACGT TGTCCAAGAC TCAACGAAAG ACTCCAACCG TTATTCATAA ACATTACCAA       120

ATACATCGCA TTAGACATTT TTACATGAGA AAAGTCAAAT TTACTCAACA GAATTACCAT       180
```

-continued

```
GATAGACTTT CACAAATTCT AACAGATTTC CCCAAATTGG ATGATATTCA TCCGTTCTAT      240

GCTGATTTGA TGAATATTCT CTACGACAAG GATCATTACA AGTTGGCTCT GGGGCAAATA      300

AATATTGCCA AAAATTTAGT GGACAATGTT GCTAAAGATT ATGTGCGACT GATGAAGTAT      360

GGCGACTCTC TCTACCGCTG CAAACAGCTG AAGCGTGCGG CCCTGGGACG GATGTGCACA      420

GTGATCAAGA GGCAGAAGCA GAGTTTGGAG TATTTGGAGC AAGTGCGTCA GCATTTATCC      480

CGTTTGCCAA CCATTGATCC GAATACCAGG ACCCTGCTTT TGTGTGGGTA CCCAAATGTT      540

GGGAAGTCCA GCTTCATCAA CAAGGTGACG AGAGCAGACG TGGATGTCCA GCCCTATGCG      600

TTCACAACCA AGTCTCTGTT TGTTGGGCAC ATGGATTATA AGTATCTACG TTGGCAGGTT      660

GTAGACACTC CTGGGATCCT GGACCACCCT CTGGAGGATA GGAACACCAT CGAGATGCAG      720

GCCATCACTG CCCTGGCCCA CCTCCGTGCT GCGGTCCTGT ATGTGATGGA TTTGTCTGAG      780

CAGTGTGGGC ATGGGCTGAG GGAACAGCTA GAACTCTTCC AGAACATCAG ACCTCTCTTC      840

ATCAACAAGC CTCTCATAGT TGTAGCCAAC AAATGTGATG TGAAGAGAAT AGCTGAACTT      900

TCTGAAGATG ATCAGAAAAT ATTTACAGAT TTGCAGTCTG AAGGATTCCC TGTAATAGAG      960

ACCAGCACCC TGACTGAGGA AGGTGTTATT AAAGTTAAAA CAGAGGCTTG CGATAGGCTT     1020

TTGGCTCATC GAGTGGAAAC CAAAATGAAG GGAAATAAAG TGAATGAGGT GCTGAATAGA     1080

CTGCACCTGG CTATCCCAAC CAGGAGGGAC GATAAGGAGA GGCCCCCTTT CATCCCTGAA     1140

GGAGTGGTGG CTCGCAGGAA GAGGATGAAA ACTGAGGAGT CCAGGAAGAA GAGGGAACGA     1200

GATCTTGAGC TGGAAATGGG AGATGATTAT ATTTTGGATC TTCAGAAGTA CTGGGATTTA     1260

ATGAATTTGT CTGAAAAACA TGATAAGATA CCAGAAATCT GGGAAGGCCA TAATATAGCT     1320

GATTATATTG ATCCAGCCAT CATGAAGAAA TTGGAAGAAT TAGAAAAAGA AGAAGAGCTG     1380

AGAACAGCTG CTGGAGAGTA TGACAGTGTA TCTGAGAGTG AAGACGAAGA GATGCTGGAA     1440

ATCCGACAGC TGGCAAAGCA AATTCGAGAG AAAAAGAAGT TGAAAATTCT GGAGTCCAAA     1500

GAAAAGAATA CACAGGGACC CAGGATGCCG CGAACTGCTA AGAAGGTTCA GAGGACAGTT     1560

TTGGAGAAGG AGATGCGTAG TCTTGGTGTT GACATGGACG ATAAAGACGA TGCCCATTAC     1620

GCAGTCCAGG CAAGAAGATC CCGGAGCATC ACTAGGAAAA GAAAGCGGGA AGACTCTGCT     1680

CCCCCGTCCT CTGTGGCCCG GAGTGGGAGT TGCTCTCGAA CTCCACGTGA CGTTTCTGGT     1740

CTTAGGGATG TCAAGATGGT GAAGAAAGCC AAGACTATGA TGAAGAATGC TCAGAAGAAG     1800

ATGAATCGGT TGGGGAAGAA AGGGGAGGCG GATAGACACG TGTTTGATAT GAAGCCCAAG     1860

CACTTGCTGT CTGGGAAGAG GAAAGCTGGT AAAAAGGACA GGAGATAGTA TCCGTTTGGT     1920

TGGCGTGGCT TCGCTAGAGT GTTGCTGTTT ATTTCCTGTT TTGGCACAGT ATGGTTTCAT     1980

GAAATTGGAG CTCTGTATAA ACTGAAAAAG ACAAAATAAG TAAAGCACTT GTTGCTTTGC     2040

TGAAAACTAT GGTTAACCCT ATATAGGTGT GGGAAATTTT TGTCACTGCA TAATATTACA     2100

AATATTTTGA GTAGACAGTG TTTCCACATT TAATGGAGTA TCAGTTGCTT CAGATTTTCA     2160

GAACTGGGAA GATTTACTGG TGTAACTGGG TTGTTTTTGA TGGAGAAAAA CCTTATTTTC     2220

TTTTGTAAGA GCTGGGAGCA AACACGTTTA TGAGTGTGTC GGAATCCCGT GCTTAAAATA     2280

CGCTCTTAAA TTATTTTCTA GTCTTATTTC ACAATGTCTC ATTGTAGTCT GTCTTCAACT     2340

ATTTTATCCA AAATANACCT CCAGAAGAAA G                                    2371
```

(2) INFORMATION FOR SEQ ID NO:2:

(i) SEQUENCE CHARACTERISTICS:

(A) LENGTH: 634 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Ala His Tyr Asn Phe Lys Lys Ile Thr Val Val Pro Ser Ala Lys
 1               5                  10                  15

Asp Phe Ile Asp Leu Thr Leu Ser Lys Thr Gln Arg Lys Thr Pro Thr
                20                  25                  30

Val Ile His Lys His Tyr Gln Ile His Arg Ile Arg His Phe Tyr Met
            35                  40                  45

Arg Lys Val Lys Phe Thr Gln Gln Asn Tyr His Asp Arg Leu Ser Gln
 50                  55                  60

Ile Leu Thr Asp Phe Pro Lys Leu Asp Asp Ile His Pro Phe Tyr Ala
 65                  70                  75                  80

Asp Leu Met Asn Ile Leu Tyr Asp Lys Asp His Tyr Lys Leu Ala Leu
                85                  90                  95

Gly Gln Ile Asn Ile Ala Lys Asn Leu Val Asp Asn Val Ala Lys Asp
            100                 105                 110

Tyr Val Arg Leu Met Lys Tyr Gly Asp Ser Leu Tyr Arg Cys Lys Gln
            115                 120                 125

Leu Lys Arg Ala Ala Leu Gly Arg Met Cys Thr Val Ile Lys Arg Gln
130                 135                 140

Lys Gln Ser Leu Glu Tyr Leu Glu Gln Val Arg Gln His Leu Ser Arg
145                 150                 155                 160

Leu Pro Thr Ile Asp Pro Asn Thr Arg Thr Leu Leu Cys Gly Tyr
                165                 170                 175

Pro Asn Val Gly Lys Ser Ser Phe Ile Asn Lys Val Thr Arg Ala Asp
            180                 185                 190

Val Asp Val Gln Pro Tyr Ala Phe Thr Thr Lys Ser Leu Phe Val Gly
            195                 200                 205

His Met Asp Tyr Lys Tyr Leu Arg Trp Gln Val Val Asp Thr Pro Gly
            210                 215                 220

Ile Leu Asp His Pro Leu Glu Asp Arg Asn Thr Ile Glu Met Gln Ala
225                 230                 235                 240

Ile Thr Ala Leu Ala His Leu Arg Ala Ala Val Leu Tyr Val Met Asp
                245                 250                 255

Leu Ser Glu Gln Cys Gly His Gly Leu Arg Glu Gln Leu Glu Leu Phe
            260                 265                 270

Gln Asn Ile Arg Pro Leu Phe Ile Asn Lys Pro Leu Ile Val Val Ala
            275                 280                 285

Asn Lys Cys Asp Val Lys Arg Ile Ala Glu Leu Ser Glu Asp Asp Gln
290                 295                 300

Lys Ile Phe Thr Asp Leu Gln Ser Glu Gly Phe Pro Val Ile Glu Thr
305                 310                 315                 320

Ser Thr Leu Thr Glu Glu Gly Val Ile Lys Val Lys Thr Glu Ala Cys
                325                 330                 335

Asp Arg Leu Leu Ala His Arg Val Glu Thr Lys Met Lys Gly Asn Lys
            340                 345                 350

Val Asn Glu Val Leu Asn Arg Leu His Leu Ala Ile Pro Thr Arg Arg
            355                 360                 365

Asp Asp Lys Glu Arg Pro Pro Phe Ile Pro Glu Gly Val Val Ala Arg

```
            370                 375                 380
Arg Lys Arg Met Glu Thr Glu Glu Ser Arg Lys Arg Glu Arg Asp
385                 390                 395                 400

Leu Glu Leu Glu Met Gly Asp Asp Tyr Ile Leu Asp Leu Gln Lys Tyr
                405                 410                 415

Trp Asp Leu Met Asn Leu Ser Glu Lys His Asp Lys Ile Pro Glu Ile
                420                 425                 430

Trp Glu Gly His Asn Ile Ala Asp Tyr Ile Asp Pro Ala Ile Met Lys
                435                 440                 445

Lys Leu Glu Glu Leu Glu Lys Glu Glu Leu Arg Thr Ala Ala Gly
450                 455                 460

Glu Tyr Asp Ser Val Ser Glu Ser Glu Asp Glu Met Leu Glu Ile
465                 470                 475                 480

Arg Gln Leu Ala Lys Gln Ile Arg Glu Lys Lys Leu Lys Ile Leu
                485                 490                 495

Glu Ser Lys Glu Lys Asn Thr Gln Gly Pro Arg Met Pro Arg Thr Ala
                500                 505                 510

Lys Lys Val Gln Arg Thr Val Leu Glu Lys Glu Met Arg Ser Leu Gly
                515                 520                 525

Val Asp Met Asp Lys Asp Asp Ala His Tyr Ala Val Gln Ala Arg
530                 535                 540

Arg Ser Arg Ser Ile Thr Arg Lys Arg Lys Glu Asp Ser Ala Pro
545                 550                 555                 560

Pro Ser Ser Val Ala Arg Ser Gly Ser Cys Ser Arg Thr Pro Arg Asp
                565                 570                 575

Val Ser Gly Leu Arg Asp Val Lys Met Val Lys Ala Lys Thr Met
                580                 585                 590

Met Lys Asn Ala Gln Lys Lys Met Asn Arg Leu Gly Lys Lys Gly Glu
                595                 600                 605

Ala Asp Arg His Val Phe Asp Met Lys Pro Lys His Leu Leu Ser Gly
                610                 615                 620

Lys Arg Lys Ala Gly Lys Lys Asp Arg Arg
625                 630

(2) INFORMATION FOR SEQ ID NO:3:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GACTCTGCTC CCCCGTCCTC TGTGGCCCGG AGTGGGAGTT GCTCTCGAAC TCCACGTGAC      60

GTTTCTGGTC TTAGGGATGT CAAGATGGTG AAGAAAGCCA AGACTATGAT GAAGAATGCT    120

CAGAAGAAGA TGAATCGGTT GGGGAAGAAA GGGGAGGCGG ATATACACTT GTTTGATATG    180

AAGCCCAAGC ACTTGCTGTC TGGGAAGAGG AAAGCTGGTA AAAGGACAG GAGATAGTAT     240

CCGTTTGGTT GGCGTGGCTT CGCTAGAGTG TTGCTGTTTA TTTCCTGGTT TGGCACAGTA    300

TGGTTTCATG AAATTGGAGC TCTGTATAAA CTGAAAAAGA CAAAATAAGT AAAGCACTTG    360

TTGCTTTGCT GAAAACTATG GTTAACCCTA TATAGGTGTG GGAAATTTTT GTCACTGCAT    420

AATATTACAA ATATTCTGAG TAGACAGTGT TTCCACATTT AATGGAGTAT CAGTTGCTTC    480
```

```
                                    -continued

AGATTTTCAG AACTGGGAAG ATTTACTGGT GTAACTGGGT TGTTTTTGAT GGAGAAAAAC      540

CTTATTTTCT TTTGTAAGAG CTGGGAGCAA ACACGTTTAT GAGTGTGTCG GAATCCCGTG      600

CTTAAAATAC GCTCTTAAAT TATTTTCTAG TCCTTATTTT ACAATGTCTC ATTGTAGTCT      660

GTCTTCAACT ATTTTATCCA AAATAAACCT CCAGAAGGAA AAAAAAAAAA AAAAAA         716

(2) INFORMATION FOR SEQ ID NO:4:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

His Glu Asp Lys Asp Asp Ala His Tyr Ala Val Gln Ala Arg Arg Ser
 1               5                  10                  15

Arg Ser Ile Thr Arg Lys Arg Lys Arg Glu Asp Ser Ala Pro Pro Ser
            20                  25                  30

Ser Val Ala Arg Ser Gly Ser Cys Ser Arg Thr Pro Arg Asp Val Ser
        35                  40                  45

Gly Leu Arg Asp Val Lys Met Val Lys Lys Ala Lys Thr Met Met Lys
    50                  55                  60

Asn Ala Gln Lys Lys Met Asn Arg Leu Gly Lys Lys Gly Glu Ala Asp
65                  70                  75                  80

Ile His Leu Phe Asp Met Lys Pro Lys His Leu Leu Ser Gly Lys Arg
                85                  90                  95

Lys Ala Gly Lys Lys Asp Arg Arg
            100

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ACCACACATC TGA                                                        13

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TGTTGGGAAC AAG                                                        13
```

CRFG-1A, A TARGET AND MARKER FOR CHRONIC RENAL FAILURE

This application is a division of application Ser. No. 09/020,466, filed Feb. 9, 1998, now U.S. Pat. No. 5,879,908, which claims the benefit of U.S. Provisional Application No. 60/045,203, filed Apr. 30, 1997, both of whose entire contents are incorporated herein by reference in their entireties. This application claims the benefit of U.S. Provisional Application No. 60/045,203. filed Apr. 30, 1997, which is herein incorporated by reference in its entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to GTP binding protein family, hereinafter referred to as chronic renal failure gene-1a (CRFG-1a). The invention also relates to inhibiting or activating the action of such polynucleotides and polypeptides.

BACKGROUND OF THE INVENTION

The sequence of CRFG-1a is similar to uncharacterized putative GTP binding proteins of yeast (YPL093w), Halobacterium cutirubrum and GTP1/OBG family of GTP binding proteins from Methanobacterium thermoautotrophicum. GTP binding proteins play important roles in intracellular transport, protein targeting and vesicle fusion.

This indicates that the GTP binding proteins family has an established, proven history as therapeutic targets. Clearly there is a need for identification and charaterization of further members of GTP binding protein family which can play a role in preventing, ameliorating or correcting dysfunctions or diseases, including, but not limited to, chronic renal disease, renal ischemia, diabetic nephropathy, acute renal failure, Neurodegenerative disease, and Azheimer's disease.

SUMMARY OF THE INVENTION

In one aspect, the invention relates to CRFG-1a polypeptides and recombinant materials and methods for their production. Another aspect of the invention relates to methods for using such CRFG-1a polypeptides and polynucleotides. Such uses include the treatment of chronic renal disease, renal ischemia, diabetic nephropathy, acute renal failure, Neurodegenerative disease, and Alzheimer's disease, among others. In still another aspect, the invention relates to methods to identify agonists and antagonists using the materials provided by the invention, and treating conditions associated with CRFG-1a imbalance with the identified compounds. Yet another aspect of the invention relates to diagnostic assays for detecting diseases associated with inappropriate CRFG-1a activity or levels.

DESCRIPTION OF THE INVENTION

Definitions

The following definitions are provided to facilitate understanding of certain terms used frequently herein.

"CRFG-1a" refers, among others, generally to a polypeptide having the amino acid sequence set forth in SEQ ID NO:2 or an allelic variant thereof.

"CRFG-1a activity or CRFG-1a polypeptide activity" or "biological activity of the CRFG-1a or CRFG-1a polypeptide" refers to the metabolic or physiologic function of said CRFG-1a including similar activities or improved activities or these activities with decreased undesirable side-effects. Also included are antigenic and immunogenic activities of said CRFG-1a.

"CRFG-1a gene" refers to a polynucleotide having the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS - STRUCTURE AND MOLECLLAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and non-protein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following: 1) Algorithm: Needleman and Wunsch, J. Mol Biol. 48: 443–453 (1970) Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

A program useful with these parameters is publicly available as the "gap" program from Genetics Computer Group, Madison Wis. The aforementioned parameters are the default parameters for polynucleotide comparisons.

Preferred polynucleotide embodiments further include an isolated polynucleotide comprising a polynucleotide having at least a 50,60, 70, 80, 85, 90, 95, 97 or 100% identity to a polynucleotide reference sequence of SEQ ID NO:1, wherein said reference sequence may be identical to the sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the numerical percent of the respective percent identity and subtracting that product from said total number of nucleotides in SEQ ID NO:1, or:

$$n_n \leq X_n - (x_n \cdot y),$$

wherein $n_n$ is the number of nucleotide alterations, $X_n$ is the total number of nucleotides in SEQ ID NO:1, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $X_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Preferred polypeptide embodiments further include an isolated polypeptide comprising a polypeptide having at least a 50,60, 70, 80, 85, 90, 95, 97 or 100% identity to a polypeptide reference sequence of SEQ ID NO:2, wherein said reference sequence may be identical to the sequence of SEQ ID NO:2 or may include up to a certain integer number of amino acid alterations as compared to the reference sequence, wherein said alterations are selected from the group consisting of at least one amino acid deletion, substitution, including conservative and nonconservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the numerical percent of the respective percent identity and subtracting that product from said total number of amino acids in SEQ ID NO:2, or:

$$n_a \le x_a - (x_a \cdot y),$$

wherein $n_a$ is the number of amino acid alterations, $x_a$ is the total number of amino acids in SEQ ID NO:2, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $X_a$ and y is rounded down to the nearest integer prior to subtracting it from $x_a$.

Polypeptides of the Invention

In one aspect, the present invention relates to CRFG-1a polypeptides (or CRFG-1a proteins). The CRFG-1a polypeptides include the polypeptide of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within CRFG-1a polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably CRFG-1a polypeptide exhibit at least one biological activity of CRFG-1a.

The CRFG-1a polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the CRFG-1a polypeptides are also included in the invention. A fragment is a polypeptide having an amino acid sequence that entirely is the same as part, but not all, of the amino acid sequence of the aforementioned CRFG-1a polypeptides. As with CRFG-1a polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of CRFG-1a polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of CRFG-1a polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate CRFG-1a activity, including those with a similar activity or an improved activity, or with a decreased undesirable activity. Also included are those that are antigenic or immunogenic in an animal, especially in a human.

Preferably, all of these polypeptide fragments retin the biological activity of the CRFG-1a, including antigenic activity. Among the most preferred fragment is that having the amino acid sequence of SEQ ID NO:4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tvr. Particularly preferred are variants in which several, 5–10, 1–5, or 1–2 amino acids are substituted, deleted, or added in any combination.

The CRFG-1a polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to CRFG-1a polynucleotides. CRFG-1a polynucleotides include isolated polynucleotides which encode the CRFG-1a polypeptides and fragments, and polynucleotides closely related thereto. More specifically, CRFG-1a polynucleotide of the invention include a polynucleotide comprising the nucleotide sequence contained in SEQ ED NO:1 encoding a CRFG-1a polypeptide of SEQ ID NO:2, and polynucleotides having the particular sequences of SEQ ID NOS:1 and 3. CRFG-1a polynucleotides further include a polynucleotide comprising a nucleotide sequence that has at least 80% identity over its entire length to a nucleotide sequence encoding the CRFG-1a polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under CRFG-1a polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such CRFG-1a polynucleotides.

CRFG-1a of the invention is structurally related to other proteins of the GTP binding protein family, as shown by the results of sequencing the cDNA encoding human CRFG-1a. The cDNA sequence of SEQ ID NO:1 contains an open reading frame (nucleotide number 3 to 1904) encoding a polypeptide of 634 amino acids of SEQ ID NO:2. The amino acid sequence of Table 1 (SEQ ID NO:2) has about 46.1% identity (using FASTA) in 634 amino acid residues with Hypothetical protein YPL093w from yeast (H. Bussey et al. Nature 387 (6632 Suppl), 103–105, 1997). The nucleotide sequence of Table 1 (SEQ ID NO:1) has about 59.7% identity (using FASTA) in 1351 nucleotide residues with Saccharomyces cerevisiae chromosome XVI cosmid 8059/8047 (H. Bussey et al. Nature 387 (6632 Suppl), 103–105, 1997). Thus, CRFG-1a polypeptides and polynucleotides of the present invention are expected to have, inter alia, similar biological functions/properties to their homologous polypeptides and polynucleotides, and their utility is obvious to anyone skilled in the art.

TABLE 1[a]

| | |
|---|---|
| AGCATGGCACATTACAACTTCAAGAAAATTACGGTGGTGC | 40 |
| CGTCCGCCAAGGACTTCATAGACCTCACGTTGTCCAAGAC | 80 |
| TCAACGAAAGACTCCAACCGTTATTCATAAACATTACCAA | 120 |
| ATACATCGCATTAGACATTTTTACATGAGAAAAGTCAAAT | 160 |
| TTACTCAACAGAATTACCATGATAGACTTTCACAAATTCT | 200 |
| AACAGATTTCCCCAAATTGGATGATATTCATCCGTTCTAT | 240 |
| GCTGATTTGATGAATATTCTCTACGACAAGGATCATTACA | 280 |
| AGTTGGCTCTGGGGCAAATAAATATTGCCAAAAATTTAGT | 320 |
| GGACAATGTTGCTAAAGATTATGTGCGACTGATGAAGTAT | 360 |
| GGCGACTCTCTCTACCGCTGCAAACAGCTGAAGCGTGCGG | 400 |
| CCCTGGGACGGATGTGCACAGTGATCAAGAGGCAGAAGCA | 440 |
| GAGTTTGGAGTATTTGGAGCAAGTGCGTCAGCATTTATCC | 480 |
| CGTTTGCCAACCATTGATCCGAATACCAGGACCCTGCTTT | 520 |
| TGTGTGGGTACCCAAATGTTGGGAAGTCCAGCTTCATCAA | 560 |
| CAAGGTGACGAGAGCAGACGTGGATGTCCAGCCCTATGCG | 600 |
| TTCACAACCAAGTCTCTGTTTGTTGGGCACATGGATTATA | 640 |
| AGTATCTACGTTGGCAGGTTGTAGACACTCCTGGGATCCT | 680 |
| GGACCACCCTCTGGAGGATAGGAACACCATCGAGATGCAG | 720 |

TABLE 1[a]-continued

| | |
|---|---|
| GCCATCACTGCCCTGGCCCACCTCCGTGCTGCGGTCCTGT | 760 |
| ATGTGATGGATTTGTCTGAGCAGTGTGGGCATGGGCTGAG | 800 |
| GGAACAGCTAGAACTCTTCCAGAACATCAGACCTCTCTTC | 840 |
| ATCAACAAGCCTCTCATAGTTGTAGCCAACAAATGTGATG | 880 |
| TGAAGAGAATAGCTGAACTTTCTGAAGATGATCAGAAAAT | 920 |
| ATTTACAGATTTGCAGTCTGAAGGATTCCCTGTAATAGAG | 960 |
| ACCAGCACCCTGACTGAGGAAGGTGTTATTAAAGTTAAAA | 1000 |
| CAGAGGCTTGCGATAGGCTTTTGGCTCATCGAGTGGAAAC | 1040 |
| CAAAATGAAGGGAAATAAAGTGAATGAGGTGCTGAATAGA | 1080 |
| CTGCACCTGGCTATCCCAACCAGGAGGGACGATAAGGAGA | 1120 |
| GGCCCCCTTTCATCCCTGAAGGAGTGGTGGCTCGCAGGAA | 1160 |
| GAGGATGGAAACTGAGGAGTCCAGGAAGAAGAGGGAACGA | 1200 |
| GATCTTGAGCTGGAAATGGGAGATGATTATATTTTGGATC | 1240 |
| TTCAGAAGTACTGGGATTTAATGAATTTGTCTGAAAAACA | 1280 |
| TGATAAGATACCAGAAATCTGGGAAGGCCATAATATAGCT | 1320 |
| GATTATATTGATCCAGCCATCATGAAGAAATTGGAAGAAT | 1360 |
| TAGAAAAAGAAGAAGAGCTGAGAACAGCTGCTGGAGAGTA | 1400 |
| TGACAGTGTATCTGAGAGTGAAGACGAAGAGATGCTGGAA | 1440 |
| ATCCGACAGCTGGCAAAGCAAATTCGAGAGAAAAAGAAGT | 1480 |
| TGAAAATTCTGGAGTCCAAAGAAAAGAATACACAGGGACC | 1520 |
| CAGGATGCCGCGAACTGCTAAGAAGGTTCAGAGGACAGTT | 1560 |
| TTGGAGAAGGAGATGCGTAGTCTTGGTGTTGACATGGACG | 1600 |
| ATAAAGACGATGCCCATTACGCAGTCCAGGCAAGAAGATC | 1640 |
| CCGGAGCATCACTAGGAAAAGAAAGCGGGAAGACTCTGCT | 1680 |
| CCCCCGTCCTCTGTGGCCCGGAGTGGGAGTTGCTCTCGAA | 1720 |
| CTCCACGTGACGTTTCTGGTCTTAGGGATGTCAAGATGGT | 1760 |
| GAAGAAAGCCAAGACTATGATGAAGAATGCTCAGAAGAAG | 1800 |
| ATGAATCGGTTGGGGAAGAAAGGGGAGGCGGATAGACACG | 1840 |
| TGTTTGATATGAAGCCCAAGCACTTGCTGTCTGGGAAGAG | 1880 |
| GAAAGCTGGTAAAAAGGACAGGAGATAGTATCCGTTTGGT | 1920 |
| TGGCGTGGCTTCGCTAGAGTGTTGCTGTTTATTTCCTGTT | 1960 |
| TTGGCACAGTATGGTTTCATGAAATTGGAGCTCTGTATAA | 2000 |
| ACTGAAAAAGACAAAATAAGTAAAGCACTTGTTGCTTTGC | 2040 |
| TGAAAACTATGGTTAACCCTATATAGGTGTGGGAAATTTT | 2080 |
| TGTCACTGCATAATATTACAAATATTTTGAGTAGACAGTG | 2120 |
| TTTCCACATTTAATGGAGTATCAGTTGCTTCAGATTTTCA | 2160 |
| GAACTGGGAAGATTTACTGGTGTAACTGGGTTGTTTTTGA | 2200 |
| TGGAGAAAAACCTTATTTTCTTTTGTAAGAGCTGGGAGCA | 2240 |
| AACACGTTTATGAGTGTGTCGGAATCCCGTGCTTAAAATA | 2280 |

TABLE 1[a]-continued

| | |
|---|---|
| CGCTCTTAAATTATTTTCTAGTCTTATTTCACAATGTCTC | 2320 |
| ATTGTAGTCTGTCTTCAACTATTTTATCCAAAATANACCT | 2360 |
| CCAGAAGAAAG | 2371 |

[a]A nucleotide sequence of a human CRFG-1a(SEQ ID NO: 1).

TABLE 2[b]

| | |
|---|---|
| MAHYNFKKITVVPSAKDFIDLTLSKTQRKTPTVIHKHYQI | 40 |
| HRIRHFYMRKVKFTQQNYHDRLSQILTDFPKLDDIHPFYA | 80 |
| DLMNILYDKDHYKLALGQINIAKNLVDNVAKDYVRLMKYG | 120 |
| DSLYRCKQLKRAALGRMCTVIKRQKQSLEYLEQVRQHLSR | 160 |
| LPTIDPNTRTLLLCGYPNVGKSSFINKVTRADVDVQPYAF | 200 |
| TTKSLFVGHMDYKYLRWQVVDTPGILDHPLEDRNTIEMQA | 240 |
| ITALAHLRAAVLYVMDLSEQCGHGLREQLELFQNIRPLFI | 280 |
| NKPLIVVANKCDVKRIAELSEDDQKIFTDLQSEGFPVIET | 320 |
| STLTEEGVIKVKTEACDRLLAHRVETKMKGNKVNEVLNRL | 360 |
| HLAIPTRRDDKERPPFIPEGVVARRKRMETEESRKKRERD | 400 |
| LELEMGDDYILDLQKYWDLMNLSEKHDKIPEIWEGHNIAD | 440 |
| YIDPAIMKKLEELEKEEELRTAAGEYDSVSESEDEEMLEI | 480 |
| RQLAKQIREKKKLKILESKEKNTQGPRMPRTAKKVQRTVL | 520 |
| EKEMRSLGVDMDDKDDAHYAVQARRSRSITRKRKREDSAP | 560 |
| PSSVARSGSCSRTPRDVSGLRDVKMVKKAKTMMKNAQKKM | 600 |
| NRLGKKGEADRRVFDMKPKHLLSGKRKAGKKDRR | 634 |

[b]An amino acid sequence of a human CRFG-1a (SEQ ID NO: 2).

One polynucleotide of the present invention encoding CRFG-1a may be obtained using standard cloning and screening, from a cDNA library derived from mRNA in cells of human kidney and testes using the expressed sequence tag (EST) analysis (Adams, M. D., etal. *Science* (1991) 252:1651–1656; Adams, M. D. et al., *Nature*, (1992) 355:632–634; Adams, M.D., et al, *Nature* (1995)377 Supp:3–174). Polynucleotides of the invention can also be obtained from natural sources such as genomic DNA libraries or can be synthesized using well known and commercially available techniques.

The nucleotide sequence encoding CRFG-1a polypeptide of SEQ ID NO:2 may be identical to the polypeptide encoding sequence contained in Table 1 (nucleotide number 3 to 1904 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of CRFG-1 a polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding CRFG-1a variants comprising the amino acid sequence of CRFG-1a polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO:3) encoding the amino acid sequence of Table 4 (SEQ ID NO:4).

TABLE 3[c]

| | | | |
|---|---|---|---|
| gACTCTGCTC | CCCCGTCCTC | TGTGGCCCGG | AgTGGGAGTT |
| GCTCTCGAAC | TCCACGTGAC | GTTTCTGGTC | TTAGGGATGT  80 |
| CAAgATGGTG | AAgAAAGCCA | AGACTATGAT | GAAGAATGCT |
| CAgAAgAAgA | TGAATCGGTT | GGGGAAgAAA | GGGGAGGCGG 160 |
| ATATACACTT | gTTTGATATG | AAGCCCAAgC | ACTTGCTGTC |
| TGGGAAgAGG | AAAGCTGGTa | AAAAGGACAG | GAGATAgTAT 240 |
| CCGTTTGGTT | GGCGTGGCTT | CGCTAgAgTG | TTGCTGTTTA |
| TTTCCTGGTT | TGGCACAGTA | TGGTTTCaTG | AAATTGGAGC 320 |
| TCTGTaTAAA | CTGAAAAAGA | CAAAATAAGT | AAAGCACTTG |
| TTGCTTTGCT | GAAAACTATG | GTTAACCCTA | TATAGGTGTG 400 |
| GGAAATTTTT | GTCaCTGCAT | AATATTACaA | ATATTCTGAG |
| TAGACAGtGT | TTCCACATTT | AATGGAGTAT | CAGTTGCTTC 480 |
| AGATTTTCAG | AACTGGGAAG | ATTTACTGGT | GTAACTGGGT |
| TGTTTTTGAT | GGAGAAAAAC | CTTATTTTCT | TTTGTAAGAG 560 |
| CTGGGAGCAA | ACACGTTTAT | GAGTGTGTCG | GAATCCCGTG |
| CTTAAAATAC | GCTCTTAAAT | tATTTTCTAG | TCCTTATTTT 640 |
| ACAATGTCTC | ATTGTAGTCT | GTCTTCAACT | ATTTTATCCA |
| AAATAAACCT | CCAGAAGGAA | AAAAAAAAAA | AAAAAA 716 |

[c]A partial nucleotide sequence of a human CRFG-1a (SEQ ID NO: 3).

TABLE 4[d]

| | |
|---|---|
| HEDKDDAHYAVQARRSRSITRKRKREDSAPPSSVARSGSC | 40 |
| SRTPRDVSGLRDVKMVKKAKTMMKNAQKKMNRLGKKGEAD | 80 |
| IHLFDMKPKHLLSGKRKAGKKDRR | 104 |

[d]A partial amino acid sequence of a human CRFG-1a (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding CRFG-1a polypeptide and to isolate cDNA and genomic clones of other genes (including genes encoding homologs and orthologs from species other than human) that have a high sequence similarity to the CRFG-1a gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding CRFG-1a polypeptide, including homologs and orthologs from species other than human, comprises the steps of screening an appropriate library under stingent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art. Thus in another aspect, CRFG-1a polynucleotides of the present invention further include a nucleotide sequence comprising a nucleotide sequence that hybridize under stringent condition to a nucleotide sequence having SEQ ID NO:1 or a fragment thereof (including that of SEQ ID NO:3). Also included with CRFG-1a polypeptides are polypeptide comprising amino acid sequence encoded by nucleotide sequence obtained by the above hybridization condition. Stringent hybridization conditions are as defined above or. alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution. 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL,* 2nd Ed., Cold Spring Harbor Laboratory Press, Cold Spring Harbor, N.Y. (1989) such as calcium phosphate transfection, DEAE-dexran mediated transfection, transvection, microinjection, cationic lipid-mediated transfection, electroporation transduction, scrape loading, ballistic introduction or infection.

Representative examples of appropriate hosts include bacterial cells, such as streptococci, staphylococci, *E. coli,* Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the CRFG-1a polypeptide is to be expressed for use in screening assays, generally, it is preferred that the polypeptide be produced at the surface of the cell. In this event, the cells may be harvested prior to use in the screening assay. If CRFG-1a polypeptide is secreted into the medium, the medium can be recovered in order to recover and purify the polypeptide; if produced intracellularly, the cells must first be lysed before the polypeptide is recovered. CRFG-1a polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of CRFG-1a polynucleotides for use as diagnostic reagents. Detection of a mutated form of CRFG-1a gene associated with a dysfunction will provide a diagnostic tool that can add to or define a diagnosis of a disease or susceptibility to a disease which results from under-expression, over-expression or altered expression of CRFG-1a. Individuals canying mutations in the CRFG-1a gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled CRFG-1a nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al, *Science* (1985) 230:1242. Sequence changes at specific locations may also be revealed by nuclease protection assays, such as RNase and S1 protection or the chemical cleavage method. See Cotton et al., *Proc Natl Acad Sci USA* ( 1985) 85: 4397–4401. In another embodiment, an array of oligonucleotides probes comprising CRFG-1a nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science,* Vol 274, pp 610–613 (1996)).

The diagnostic assays offer a process for diagnosing or determining a susceptibility to chronic renal disease, renal ischemia, diabetic nephropathy, acute renal failure, Neurodegenerative disease. and Alzheimer's disease through detection of mutation in the CRFG-1a gene by the methods described.

In addition, chronic renal disease, renal ischemia, diabetic nephropathy, acute renal failure, Neurodegenerative disease, and Alzheimer's disease, can be diagnosed by methods comprising determining from a sample derived from a subject an abnormally decreased or increased level of CRFG-1a polypeptide or CRFG-1a mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an CRFG-1a polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly chronic renal disease, renal ischemia, diabetic nephropathy, acute renal failure, Neurodegenerative disease, and Atzheimer's disease, which comprises:

(a) a CRFG-1a polynucleotide, preferably the nucleotide sequence of SEQ ID NO:1, or a fragment thereof;
(b) a nucleotide sequence complementary to that of (a);
(c) a CRFG-1a polypeptide, preferably the polypeptide of SEQ ID NO:2, or a fragment thereof; or
(d) an antibody to a CRFG-1a polypeptide, preferably to the polypeptide of SEQ ID NO:2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

The CRFG-1a gene (SEQ ID NO:1) is found on chromosome 10p15.2–15.3 which is associated with glioma of the brain.

Antibodies

The polypeptides of the invention or their fragments or analogs thereof, or cells expressing them can also be used as immunogens to produce antibodies immunospecific for the CRFG-1a polypeptides. The term "immunospecific" means that the antibodies have substantially greater affinity for the polypeptides of the invention than their affinity for other related polypeptides in the prior art.

Antibodies generated against the CRFG-1a polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al, *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against CRFG-1a polypeptides may also be employed to treat chronic renal disease, renal ischemia, diabetic nephropathy, acute renal failure, Neurodegenerative disease, and Alzheimer's disease, among others.

Vaccines

Another aspect of the invention relates to a method for inducing an immunological response in a mammal which comprises inoculating the mammal with CRFG-1a polypeptide, or a fragment thereof, adequate to produce antibody and/or T cell immune response to protect said animal from chronic renal disease, renal ischemia, diabetic nephropathy, acute renal failure, Neurodegenerative disease, and Alzheimer's disease, among others. Yet another aspect of the invention relates to a method of inducing immunological response in a mammal which comprises, delivering CRFG-1a polypeptide via a vector directing expression of CRFG-1a polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a CRFG-1a polypeptide wherein the composition comprises a CRFG-1a polypeptide or CRFG-1a gene. The vaccine formulation may further comprise a suitable carrier. Since CRFG-1a polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The CRFG-1a polypeptide of the present invention may be employed in a screening process for compounds which activate (agonists) or inhibit activation of (antagonists, or otherwise called inhibitors) the CRFG-1a polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., Current Protocols in Immunology 1(2):Chapter5 (1991).

CRFG-1a polypeptides are responsible for many biological functions, including many pathologies. Accordingly, it is desirous to find compounds and drugs which stimulate CRFG-1a polypeptide on the one hand and which can inhibit the function of CRFG-1a polypeptide on the other hand. In general, agonists are employed for therapeutic and prophylactic purposes for such conditions as chronic renal disease, renal ischemia, diabetic nephropathy, acute renal failure, Neurodegenerative disease, and Alzheimer's disease. Antagonists may be employed for a variety of therapeutic and prophylactic purposes for such conditions as chronic renal disease, renal ischernia, diabetic nephropathy, acute renal failure, Neurodegenerative disease, and Alzheimer's disease.

In general, such screening procedures may involve using appropriate cells which express the CRFG-1a polypeptide or respond to CRFG-1a polypeptide of the present invention. Such cells include cells from mammals, yeast, Drosophila or E. coli. Cells which express the CRFG-1a polypeptide (or cell membrane containing the expressed polypeptide) or respond to CRFG-1a polypeptide are then contacted with a test compound to observe binding, or stimulation or inhibition of a functional response. The ability of the cells which were contacted with the candidate compounds is compared with the same cells which were not contacted for CRFG-1a activity.

The assays may simply test binding of a candidate compound wherein adherence to the cells bearing the CRFG-1a polypeptide is detected by means of a label directly or indirectly associated with the candidate compound or in an assay involving competition with a labeled competitor. Further, these assays may test whether the candidate compound results in a signal generated by activation of the CRFG-1a polypeptide, using detection systems appropriate to the cells bearing the CRFG-1a polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a CRFG-1a polypeptide to form a mixture, measuring CRFG-1a activity in the mixture, and comparing the CRFG-1a activity of the mixture to a standard.

The CRFG-1a cDNA, protein and antibodies to the protein may also be used to configure assays for detecting the effect of added compounds on the production of CRFG-1a mRNA and protein in cells. For example, an ELISA may be constructed for measuring secreted or cell associated levels of CRFG-1a protein using monoclonal and polyclonal antibodies by standard methods known in the art, and this can be used to discover agents which may inhibit or enhance the production of CRFG-1a (also called antagonist or agonist, respectively) from suitably manipulated cells or tissues.

The CRFG-1a protein may be used to identify membrane bound or soluble receptors, if any, through standard receptor binding techniques known in the art. These include, but are not limited to, ligand binding and crosslinking assays in which the CRFG-1a is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of CRFG-1a which compete with the binding of CRFG-1a to its receptors, if any. Standard methods for conducting screening assays are well understood in the art.

Examples of potential CRFG-1a polypeptide antagonists include antibodies or, in some cases, oligonucleotides or proteins which are closely related to the ligands, substrates, enzymes, receptors, etc., as the case may be, of the CRFG-1a polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for CRFG-1a polypeptides; or compounds which decrease or enhance the production of CRFG-1a polypeptides, which comprises:

(a) a CRFG-1a polypeptide, preferably that of SEQ ID NO:2;

(b) a recombinant cell expressing a CRFG-1a polypeptide, preferably that of SEQ ID NO:2;

(c) a cell membrane expressing a CRFG-1a polypeptide; preferably that of SEQ ID NO:2: or (d) antibody to a CRFG-1a polypeptide, preferably that of SEQ ID NO:2. It will be appreciated that in any such kit, (a), (b), (c) or (d) may comprise a substantial component.

Prophylactic and Therapeutic Methods

This invention provides methods of treating abnormal conditions such as, chronic renal disease, renal ischemia, diabetic nephropathy, acute renal failure, Neurodegenerative disease, and Alzheimer's disease, related to both an excess of and insufficient amounts of CRFG-1a polypeptide activity.

If the activity of CRFG-1a polypeptide is in excess, several approaches are available. One approach comprises administering to a subject an inhibitor compound (antagonist) as hereinabove described along with a pharmaceutically acceptable carrier in an amount effective to inhibit the function of the CRFG-1a polypeptide, such as, for example, by blocking the binding of ligands, substrates, enzymes, receptors, etc., or by inhibiting a second signal, and thereby alleviating the abnormal condition. In another approach, soluble forms of CRFG-1a polypeptides still capable of binding the ligand, substrate, enzymes, receptors, etc. in competition with endogenous CRFG-1a polypeptide may be administered. Typical embodiments of such competitors comprise fragments of the CRFG-1a polypeptide.

In another approach, soluble forms of CRFG-1a polypeptides still capable of binding the ligand in competition with endogenous CRFG-1a polypeptide may be administered. Typical embodiments of such competitors comprise fragments of the CRFG-1a polypeptide.

In still another approach, expression of the gene encoding endogenous CRFG-1a polypeptide can be inhibited using expression blocking techniques. Known such techniques involve the use of antisense sequences, either internally generated or separately administered. See, for example, O'Connor, *J Neurochem* (1991) 56:560 in *Olizodeoxvnucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al, *Science* (1988) 241:456; Dervan et al., *Science* (1991) 251:1360. These oligomers can be administered per se or the relevant oligomers can be expressed in vivo.

For treating abnormal conditions related to an underexpression of CRFG-1a and its activity, several approaches are also available. One approach comprises administering to a subject a therapeutically effective amount of a compound which activates CRFG-1a polypeptide, i.e., an agonist as described above, in combination with a pharmaceutically acceptable carrier, to thereby alleviate the abnormal condition. Alternatively, gene therapy may be employed to effect the endogenous production of CRFG-1a by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of CRFG-1a polypeptides in combination with a suitable pharmaceutical carrier.

Formulation and Administration

Peptides, such as the soluble form of CRFG-1a polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Two animal model systems have been studied to provide targets for intervention in chronic renal failure. CRFG-1a is a novel gene identified by differential display PCR to be down regulated in three animal models of chronic renal failure, the obese Zucker rat and the ⅚ nephrectomized rat. In addition, aged Fisher 344 rats (24 months old), which have enlarged kidneys and reduced renal function, also have decreased expression of CRFG-1a. Loss of expression of this gene in renal failure may indicate an important role in normal functioning of the kidney.

In 5-month old obese Zucker rats, that have developed chronic renal failure, CRFG-1a mRNA is decreased to less than ⅓ of levels seen in lean and healthy age-matched controls. Because there is no correlation of proteinuria with CRFG-1a expression, a decrease in CRFG-1a is an early marker of renal impairment before standard clinical indicators.

While in the rat, CRFG-1a has 2 mRNA sizes of 2.5 and 1.5 kb, in the human only one molecular weight species is identified at 2.7 kb. Human CRFG-1a was mapped to human chromosome 10p15.2–15. This region of chromosome 10 is linked to 171840 PHOSPHOFRUCTOKINASE, PLATELET TYPE, 600449 DIHYDRODIOL DEHYDROGENASE, TYPE I; 601070 INTERLEUKIN-15 RECEPTOR, ALPHA; 600448 PROTEIN KINASE C, THETA FORM; 147270 INTER-ALPHA-TRYPSIN INHIBITOR, HEAVY CHAIN-1; 176870 PROTEIN HC; 137800 GLIOMA OF BRAIN, 300007 INTERLEUKIN-9 RECEPTOR; and 147680 INTERLEUKIN-2.

Normal mRNA expression on a multiple tissue northern blot identifies expression in skeletal muscle>testes>pancreas>heart>thymus>placenta>kidney>leukocytes>spleen>ovary>colon>brain>prostate.

EXAMPLE 1:

The existence of CRFG-1a was determined by differential display polymerase chain reaction (DDPCR) as developed by Liang P. and Pardee A. B. *Science.* Aug. 14, 1992; Volume 257, pages 967–71. An oligonucleotide primer (Primer I), 5'-ACCACACATCTGA-3' (SEQ ID NO:5) was used in the synthesis of complementary DNA (cDNA) from RNA of lean and obese Zucker rat kidneys. cDNA was synthesized in a 20 $\mu$l volume with 0.5 $\mu$g RNA, 1 $\mu$M primer I, 20 $\mu$M dNTP, 400 units M-MLV reverse transcriptase (Promega, Madison, Wis.), and 1× standard reverse transcriptase buffer as given by the manufacturer. The reaction sample was heated to 65 degrees C. for 5 minutes and then incubated at 42 degrees C. for one hour. Polymerase chain reaction (PCR) was then performed in a 20 $\mu$l reaction volume using 4 $\mu$l of the cDNA synthesis reaction from above with 1.5 mM $MgCl_2$, 20 $\mu$M DNTP, 1 $\mu$M primer I, 1 $\mu$M primer II (5'-TGTTGGGAACAAG -3') (SEQ ID NO:6), 2 $\mu$Ci [33-P]-d-alpha-ATP, 1.25 U Amplitaq polymerase (Perkin Elmer, Foster City, Calif.) and 1× standard PCR buffer from the manufacturer. PCR cycling conditions were 40 cycles of 94° C. for 30 seconds, 42° C. for 2 minutes, 72° C. for 30 seconds with a final extension of 72° C. for 5 minutes. Labeled PCR fragments from lean and obese Zucker rat Kidney RNA were resolved on a 12% SDS-polyacrylamide gel and exposed to X-ray film for 16 hours. A PCR amplified DNA fragment of 225 nucleotides was identified to be decreased in obese Zucker rat kidneys compared to lean age matched control rats. The fragment was excised from the dried polyacrylamide gel and DNA was eluted with boiling water. The eluted DNA was subjected to PCR using the same conditions as above. A 2 $\mu$l aliquot of the PCR reaction was then used to subclone the PCR fragment into the pCRII vector (Invitrogen, Carlsbad, Calif.) using standard reaction conditions of the manufacturer. The cDNA insert was then sequenced with the fmol sequencing kit (Promega, Madison, Wis.).

The sequence information was used to generate an antisense primer for the cloning of additional 5' sequence using the Marathon RACE kit (Clonetech, Palo, Alto, Calif.). The 607 nucleotide sequence obtained from the Marathon RACE kit was then used to identify the human homologue using the BLAST sequence analysis algorithm. The full length human cDNA was cloned from kidney mRNA using the Marathon Race kit. The human sequence is given in SEQ ID NO:1.

EXAMPLE 2

CRFG-1a mRNA was detected by northern blot in RNA from rat kidneys. Total RNA was extracted from renal cortex by guanidinium thiocyanate denaturation and acidified phenol-chloroform extraction (CHOMCZYNSKI P, SACCHI N: *Analyt Biochem* 162:156–159, 1987). Total RNA (10 $\mu$g) was fractionated on 0.2M formaldehyde- 1% agarose gels and transferred to nylon membranes (Nylon-1, Gibco-BRL, Gaithersburg, Md.) in 4× standard saline citrate. Equivalent loading and transfer were verified by methylene blue staining. Antisense [32P]cDNA probes were made for CRFG-1a that recognizes mRNA from rat at 1.5 and 2.5 kb. Northern blot analysis showed that CRFG-1a mRNA was decreased in kidneys from obese Zucker rats which develop renal failure. CRFG-1a mRNA was also decreased in kidneys after partial nephrectomy where ⅚ of the total renal mass was removed. This animal model develops chronic renal disease (Shea S M, Raskova J, Morrison AB *Am J Pathol* 1980 Aug; 100(2):513–528 ). CRFG-1a mRNA was also decreased in kidneys of aging F344 rats. F344 rats develop renal disease with advancing age (McDermott G F, Ingram A, Scholey J, Kirkland JL, Whiteside C I *J Gerontol A Biol Sci Med Sci* 1996 Mar; 51(2):M80–M85), suggesting that CRFG-1a is decreased in renal disease.

All publications, including but not limited to patents and patent applications, cited in this specification are herein incorporated by reference as if each individual publication were specifically and individually indicated to be incorporated by reference herein as though fully set forth.

What is claimed is:

1. An isolated CRFG-1a polypeptide comprising an amino acid sequence which is at least 80% identical to the amino acid sequence depicted in SEQ ID NO:2 over its entire length.

2. The polypeptide of claim 1 which comprises the amino acid sequence of SEQ ID NO:2.

* * * * *